(12) United States Patent
Stock et al.

(10) Patent No.: US 7,329,390 B2
(45) Date of Patent: Feb. 12, 2008

(54) DEVICE AND PROCESS FOR MEASURING BREATH ALCOHOL

(75) Inventors: Burkhard Stock, Lübeck (DE); Dieter Krüger, Lübeck (DE); Rigobert Chrzan, Bad Oldesloe (DE); Hans-Jürgen Busack, Lübeck (DE)

(73) Assignee: Drager Safety AG & Co. KGaA, Lübeck (DE)

( * ) Notice: Subject to any disclaimer, the term of this patent is extended or adjusted under 35 U.S.C. 154(b) by 703 days.

(21) Appl. No.: 10/385,796

(22) Filed: Mar. 11, 2003

(65) Prior Publication Data

US 2003/0228702 A1 Dec. 11, 2003

(30) Foreign Application Priority Data

Jun. 11, 2002 (DE) .............................. 102 25 815

(51) Int. Cl.
*G01N 33/497* (2006.01)
*A61B 5/097* (2006.01)

(52) U.S. Cl. .................. 422/84; 73/23.3; 436/900; 600/532

(58) Field of Classification Search ............... 422/84; 73/23.3; 436/900; 600/532
See application file for complete search history.

(56) References Cited

U.S. PATENT DOCUMENTS

| | | | |
|---|---|---|---|
| 3,780,311 A * | 12/1973 | Brown ...................... 307/10.6 |
| 3,785,774 A * | 1/1974 | Murphy ...................... 422/84 |
| 3,830,596 A * | 8/1974 | Kondo ...................... 417/413.1 |
| 4,300,384 A | 11/1981 | Wiesner et al. |
| 4,707,336 A | 11/1987 | Jones |
| 4,736,619 A | 4/1988 | Legrand |
| 4,809,810 A | 3/1989 | Elfman et al. |
| 5,111,827 A | 5/1992 | Rantala |
| 5,363,857 A | 11/1994 | Howard |
| 5,369,977 A * | 12/1994 | Rhodes et al. ............... 73/23.3 |
| 5,398,695 A * | 3/1995 | Anderson et al. ........... 600/532 |
| 5,426,415 A | 6/1995 | Prachar et al. |
| 6,134,462 A | 10/2000 | Rantala |
| 6,167,746 B1 | 1/2001 | Gammenthaler |
| 6,241,950 B1 * | 6/2001 | Veelenturf et al. .......... 422/103 |
| 6,289,718 B1 | 9/2001 | Stock |
| 2002/0137227 A1 * | 9/2002 | Weckstrom ................. 436/172 |

FOREIGN PATENT DOCUMENTS

DE 2 035 982 1/1972

(Continued)

*Primary Examiner*—Jill Warden
*Assistant Examiner*—Paul S Hyun
(74) *Attorney, Agent, or Firm*—McGlew and Tuttle, P.C.

(57) ABSTRACT

A breath alcohol measuring device includes a flow chamber, for receiving exhaled breathing gas of a person, with a flow diaphragm. A differential pressure sensor has a first measuring connection via a first gas line (5) to the interior space of the flow chamber (2) upstream of the flow diaphragm (3), and a second measuring connection via second and third gas lines (12, 15) and a breath alcohol sensor (8) to the interior space of the flow chamber (2) downstream of the flow diaphragm (3). A throttling element (14) is present in the second gas line (12). The second gas line (12) is connected to a sampling system (9, 10), and an evaluating and control unit (6) is connected to the sensors (4, 8) and to the sampling system (9, 10) for controlling the sampling system.

18 Claims, 1 Drawing Sheet

FOREIGN PATENT DOCUMENTS

| | | |
|---|---|---|
| DE | 43 00 029 | 7/1994 |
| DE | 195 45 794 | 6/1997 |
| DE | 199 41 586 | 3/2001 |
| EP | 0 510 484 | 10/1992 |
| EP | 0 627 195 | 12/1994 |
| WO | WO 90/02331 | 3/1990 |

* cited by examiner

DEVICE AND PROCESS FOR MEASURING BREATH ALCOHOL

FIELD OF THE INVENTION

The present invention pertains to a device and process for measuring breath alcohol, in particular where a pressure drop is measured across a restriction in the breath flow. A sample is withdrawn from the breath flow to measure the alcohol and test for proper operation.

BACKGROUND OF THE INVENTION

Breath alcohol measurements have been known per se and are carried out with various different measuring devices and methods. For example, U.S. Pat. No. 6,167,746 B1 shows a measuring device that comprises a measuring tube, to which a pressure sensor and a temperature sensor as well as a gas sampling valve with an electrochemical measuring cell arranged downstream of the valve for the measurement of the breath alcohol concentration are connected one after another in the direction of flow of the gas.

Prior-art breath alcohol measuring devices, e.g., the Alcotest® devices, have been used for some years for the specific monitoring of the breath alcohol concentration of drivers especially during traffic checks.

Breath alcohol measuring devices are also used in combination with so-called "interlock" systems in private motor vehicles to prevent driving under the influence of alcohol. The alcohol test in these applications is not performed under the supervision of authorized persons. It is therefore especially important in these "interlock" systems either to rule out attempts at manipulating with the breath alcohol measurement and/or to have the possibility of detecting such attempts by recording characteristic measured variables, e.g., during the reading of the operating data at an authorized service station. The result of the measurement for the breath alcohol concentration can be manipulated, e.g., by passing the breathing air over a wash bottle or through filter materials, by sending air from an air reservoir into the measuring device or the like.

SUMMARY AND OBJECTS OF THE INVENTION

The object of the present invention is to provide an improved device and a process for breath alcohol measurement, so that errors in function or operation of the measurement can be recognized, and more accurate measurement results can be obtained.

This object is accomplished with a flow chamber receivable of a flow of the gas. A flow chamber restriction is arranged in the flow chamber and divides the gas into upstream and downstream gas. The flow chamber restriction causes a pressure drop in the flow of the gas as the gas flows through the flow chamber. A gas concentration sensor is in communication with the flow chamber. A sample system is in communication with the flow chamber through the gas sensor and pulls gas from the flow chamber into the gas sensor. A throttling element is arranged between the gas sensor and the sample system.

A differential pressure sensor is connected upstream and downstream of the flow restriction and measures a pressure difference between the upstream gas and the downstream gas. One of the upstream and downstream gas is measured through the gas sensor. A control unit receives pressure and gas signals from the pressure sensor and the gas sensor, and controls the sample system. A temperature sensor is arranged in the flow chamber downstream of the flow chamber restriction and is connected to the control unit.

The sampling system is pre-operated before the measuring of the alcohol to test if the device is operating properly. The pressures measured during the pre-operation are compared with predetermined reference values to determine proper or altered operation. The temperature and temperature changes during operation are also compared to predetermined temperature reference values to determine proper operation.

An essential advantage of the device according to the present invention is the possibility of detecting various dysfunctions and operating states by means of a single device with the indicated connection of the components.

An additional advantage is obtained when devices according to the present invention are used in motor vehicles, aircraft or watercraft to block the operation as a function of the breath alcohol concentration of the operator, which was measured previously. As an alternative, the starter of a driving engine is released for operation only when the comparison of the measured value or values for the breath alcohol concentration with preset reference values shows that the latter are not exceeded. In the broadest sense of the word, the present invention can be used such that a machine, e.g., an engine or a closing device is either released for operation by an upstream breath alcohol measuring device and as a function of the result of a breath alcohol measurement of an operator and after comparison with preset reference values, namely, when the reference values are not exceeded, or it is blocked for the further operation, namely, if preset reference values are exceeded after measurement at a given point in time or at different points in time after an initial release of the operation of the machine.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE schematically shows a device according to the present invention.

DESCRIPTION OF THE PREFERRED EMBODIMENT

Figure 1:
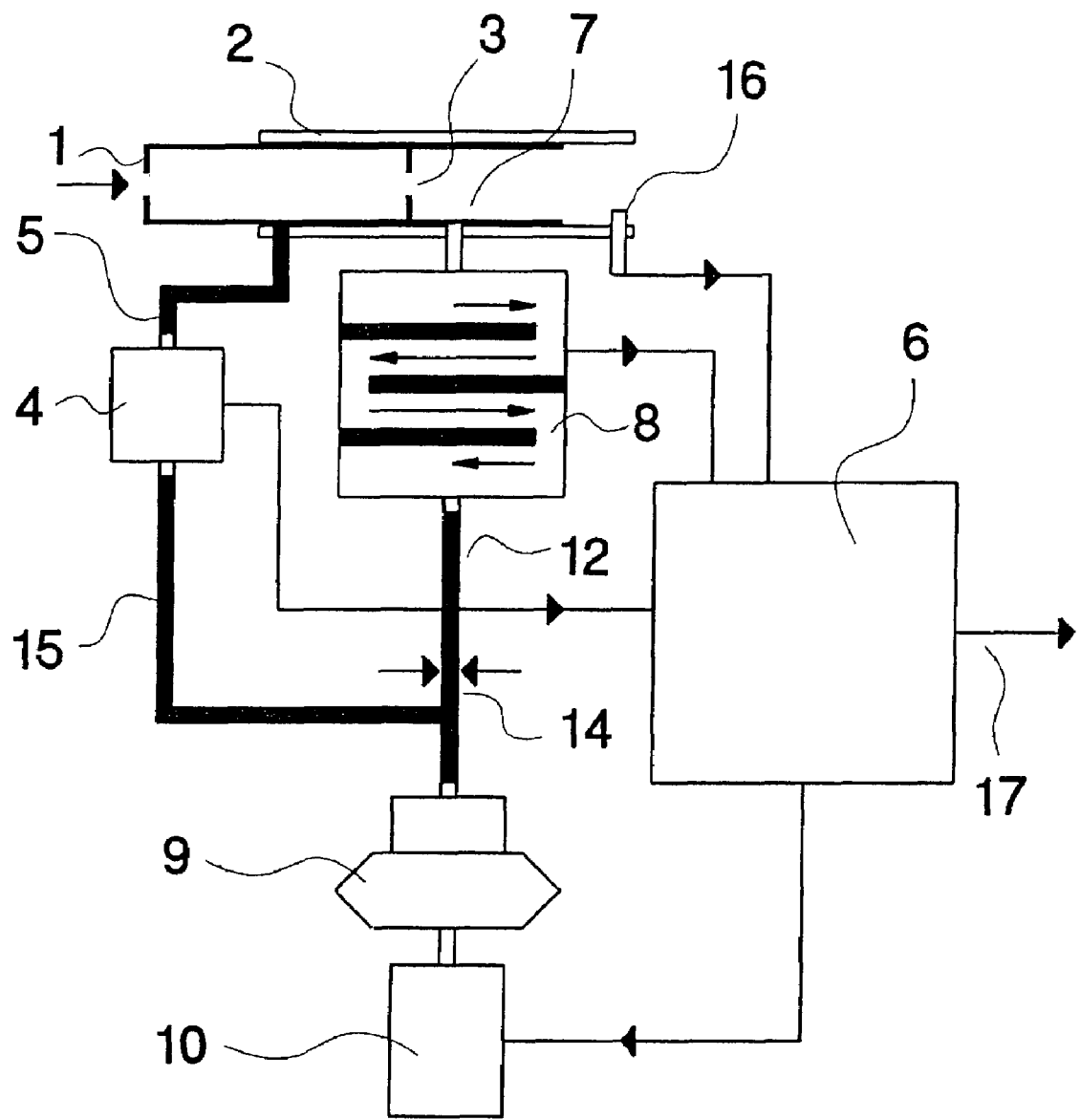

A replaceable mouthpiece 1 is inserted into the tubular flow chamber 2. A person to be tested, whose breath alcohol concentration is to be measured, blows into the mouthpiece. At the flow diaphragm 3 with a circular flow cross section of about 3 mm to 4 mm, the "flow" (breathing gas volume flow) generates a pressure drop, which strictly depends on the flow. The pressure drop is measured with a differential pressure sensor 4, whose first measuring connection is connected via a first gas line 5 to the mouthpiece 1 via the interior space of the flow chamber 2 upstream of the flow diaphragm or restriction 3. The second measuring connection of the differential pressure sensor 4 is via the breath alcohol sensor 8 and thus it has a connection to the interior space of the flow chamber 2 downstream, i.e., behind the flow diaphragm 3. The evaluating and control unit 6 calculates from the measured differential pressure signal the breathing gas volume flow, which flows through the mouthpiece 1 and the flow chamber 2, and it calculates from this by integration over time the breathing gas volume released by the person being tested. The inlet pipe connection 7 of the breath alcohol sensor 8, through which a sample of the breathing gas flow is taken into the breath alcohol sensor 8 by means of a sampling system 9, 10 comprising the elastic bellows 9 and the pressing magnet 10 as soon as the person, whose breath alcohol concentration is to be measured, has released a certain minimum breathing gas volume, is located behind, i.e., downstream of the flow diaphragm 3.

To start the sampling, the evaluating and control unit 6 sends a current pulse to the pressing magnet 10, which compresses the bellows 9 as a result. After the current has been switched off, the bellows 9 is released and draws a volume of air, which is determined by the design, through the breath alcohol sensor 8, where the alcohol is rapidly absorbed by the sensor surface of an electrochemical gas sensor, which is preferably used, and leads to a concentration-dependent measured signal for the breath alcohol content of the person being tested due to a characteristic electrochemical detection reaction, and can be used further in the known manner.

Via a second gas line 12, the breath alcohol sensor 8 is connected to the sampling system 9, 10. A throttling element 14 with a cross section of a diameter of barely 1 mm is located in the second gas line 12, and a pressure change takes place at the throttling element 14 when the bellows 9 is compressed or released. Such pressure changes reach the second measuring connection of the differential pressure sensor 4 via the third gas line 15 and can thus be measured.

The temperature sensor 16 arranged downstream of the flow diaphragm 3 at the outlet of the measuring chamber 2 is used to check whether breathing gas is indeed flowing through the mouthpiece 1 and the measuring chamber 2. To perform this check, a measurement is performed to determine whether the temperature changes at the temperature sensor 16 when the differential pressure sensor 4 indicates that a "flow" is present.

In a preferred embodiment of the breath alcohol measuring device, the evaluating and control unit 6 is connected on the output side via a signal connection 17 to a machine or device, which is to be operated by a person and whose operation is either released or blocked as a function of the breath alcohol concentration of the person being tested, which concentration was measured before in the breath alcohol measuring device, and after comparison with corresponding reference values by the evaluating and control unit 6. In particular, the starter of a motor vehicle, aircraft or watercraft is released via the signal connection 17 only when the measured breath alcohol level is below a preset limit value or at least does not exceed it. As an alternative, the machine to be operated, especially the starter or the driving engine, is blocked for the further operation when preset reference values for the breath alcohol concentration are exceeded at a certain point in time or at different points in time after a initial release of the operation of the machine.

Before the sampling and measurement of the breath alcohol content proper, the breath alcohol measuring device performs a check to determine whether the sampling system 9, 10 is able to function properly. To do so, the measured signal of the differential pressure sensor 4 is evaluated by the evaluating and control unit 6. The bellows 9 is compressed by switching on the current for the pressing magnet 10. The current is switched off after about 100 msec and the bellows 9 is released. The measured differential pressure first rises steeply over time due to the rapid compression, passes through a characteristic maximum and then returns toward zero when the pressing magnet 10 has reached its end stop. If the bellows 9 is subsequently released, a vacuum is generated at the flow diaphragm 3, which has a time curve similar to that of the compression pulse, but with a negative pressure deviation. The release process is concluded when the bellows 9 is completely released. The maximum of the compression pulse determined on the basis of the measured differential pressure is markedly higher than the release pulse, which is likewise determined on the basis of the measured differential pressure, because the force compressing the bellows 9 is stronger than the restoring force of the bellows.

To test the function of the sampling system 9, 10, a check is performed by the evaluating and control unit 6 by comparison with stored reference signals to determine whether both the compression signal and the release signal are present. If, e.g., the compression pulse is missing after the current has been switched on or it is markedly lower than the reference signal, i.e., e.g., lower than 50%, the bellows 9 has not moved or it possibly has a leak. If a compression pulse is present but the release pulse is not, the bellows 9 is stuck at the stop. The evaluating and control unit 6 sends an error report in both cases. Another possibility of error that should be detected arises when the inlet pipe connection 7 of the breath alcohol sensor 8 is blocked due to manipulation or contamination. In this case, no sample is taken from the breathing flow to the breath alcohol sensor 8 when the sampling system 9, 10 is actuated, so that the time-dependent differential pressure curves of the bellows 9, which are measured with the differential pressure sensor 4, will markedly deviate from the normal case. Since the amount of compressed gas cannot escape, a higher maximum pressure builds up, and it drops again only when the current of the pressing magnet 10 is interrupted after about 100 msec and the bellows 9 is released. The exact pressure curve depends on how tight the inlet pipe connection 7 is in reality. An inadmissible sampling is defined, e.g., such that the half-width value of the compression pulse must not exceed a stored reference value. Another possibility of deliberate manipulation with the breath alcohol measuring device is the closing of the outlet opening of the flow chamber 2 in order to build up a static pressure without a "flow" being present. However, since the pressure will now act on both measuring connections of the differential pressure sensor 4, no measured signal is generated, and no "flow" is consequently recognized, either, so that no sampling or measurement will take place. This is another essential advantage of the device according to the present invention.

Another possibility of deliberate manipulation, namely, the closing of the flow diaphragm 3 in the flow chamber 2, can be recognized by the measuring system by means of a temperature sensor 16, which is preferably used. A pressure is generated in the front part of the flow chamber 2 in the case of this possibility of manipulation without breathing air reaching the inlet pipe connection 7 of the breath alcohol sensor 8. The differential pressure sensor 4 detects a differential pressure in this case, so that a "flow" is assumed, as during a normal measurement. If the sampling is started by the evaluating and control unit 6 after a minimum volume has been reached, only outside air will reach the breath alcohol sensor 8. Consequently, the temperature sensor 16 is used to determine whether breathing air is flowing into the rear, downstream part of the flow chamber 2. The temperature is measured for this purpose immediately before the breathing gas sample is released by the person to be tested in the flow chamber 2 and the time-dependent temperature curve is then measured during the expiration. Experience has shown that the breathing gas temperature is never constant during the expiration process, so that even a slight temperature change detected by less than 1° C. means that expired gas is flowing past the temperature sensor 16 and consequently also the inlet pipe connection 7 of the breath alcohol sensor 8. Conversely, no temperature change is measured when the flow diaphragm 3 is closed.

While specific embodiments of the invention have been shown and described in detail to illustrate the application of the principles of the invention, it will be understood that the invention may be embodied otherwise without departing from such principles.

What is claimed is:

1. A device for measuring breath alcohol, the device comprising:
   a flow chamber receiving exhaled breathing gas flow of a test subject;
   a flow diaphragm arranged in said flow chamber for flow through said flow diaphragm from an upstream side of said flow diaphragm to a downstream side of said flow diaphragm;
   a first gas line in communication with an interior space of said flow chamber upstream of said flow diaphragm;
   a breath alcohol sensor in communication with an interior space of said flow chamber downstream of said flow diaphragm;
   a second gas line in communication with said breath alcohol sensor;
   a differential pressure sensor bridging over said flow diaphragm, a first measuring connection of said differential pressure sensor being connected to said first gas line, a second measuring connection of said differential pressure sensor being connected through said second gas line and said breath alcohol sensor to said interior space of said flow chamber downstream of said flow diaphragm;
   a throttling element arranged in said second gas line;
   a sampling system connected to said second gas line, said sampling system generating suction for pulling a gas sample into said breath alcohol sensor and toward or into said second gas line; and
   an evaluating and control unit connected on an input side to said pressure and alcohol sensors and receiving measured signals of said sensors, said evaluating and control unit being connected on an output side to said sampling system for controlling said sampling system.

2. A device in accordance with claim 1, further comprising:
   a temperature sensor arranged in an outlet area of said flow chamber downstream of said flow diaphragm, said temperature sensor being connected to said evaluating and control unit for transmitting measured temperature values.

3. A device in accordance with claim 1, wherein:
   said sampling system comprises an electrically driven pumping element.

4. A device in accordance with claim 2, wherein:
   said sampling system comprises an electrically driven pumping element, with a bellows actuated by a pressing magnet.

5. A device in accordance with claim 1, wherein:
   said evaluating and control unit has a signal connection on said output side to selectively release and block operation of a machine or device.

6. A device in accordance with claim 2, wherein:
   said evaluating and control unit has a signal connection on said output side to selectively release and block operation of a machine or device.

7. A device in accordance with claim 5, wherein:
   said machine or device is a starter of a driving engine of a motor vehicle, aircraft or watercraft.

8. A device in accordance with claim 6, wherein:
   said machine or device is a starter of a driving engine of a motor vehicle, aircraft or watercraft.

9. A device in accordance with claim 1, wherein:
   said breath alcohol sensor is one of an electrochemical, semiconductor or infrared optical sensor.

10. A breath alcohol measuring device comprising:
    a flow tube having an inlet and an outlet with a flow chamber between said inlet and said outlet, said flow chamber receiving exhaled breathing gas flow of a person being tested;
    a flow restriction wall with a flow opening for flow through said flow restriction wall from an upstream side of said flow restriction wall to a downstream side of said flow restriction wall, said flow restriction wall with flow opening causing a pressure drop in the flow of the gas from said upstream side to said downstream side;
    a first gas line in fluid communication with said flow chamber upstream of said flow restriction wall;
    a breath alcohol sensor in fluid communication with said flow chamber downstream of said flow restriction wall;
    a second gas line in communication with said breath alcohol sensor;
    a differential pressure sensor bridging over said flow restriction wall, a first measuring connection of said differential pressure sensor being connected to said first gas line and a second measuring connection of said differential pressure sensor being connected through said second gas line and said breath alcohol sensor to said interior space of said flow tube downstream of said flow restriction wall;
    a sampling system connected to said second gas line, said sampling system generating suction for pulling a gas sample into said breath alcohol sensor and toward or into said second gas line; and
    an evaluating and control unit connected on an input side to said pressure and alcohol sensors and receiving measured signals of said sensors, said evaluating and control unit being connected on an output side to said sampling system for controlling said sampling system.

11. A breath alcohol measuring device in accordance with claim 10, further comprising:
    a temperature sensor arranged adjacent to said outlet of said flow chamber downstream of said flow restriction wall, said temperature sensor being connected to said evaluating and control unit for transmitting measured temperature values.

12. A breath alcohol measuring device in accordance with claim 10, further comprising a throttling element arranged in said second gas line, wherein said sampling system comprises an electrically driven pumping element.

13. A breath alcohol measuring device in accordance with claim 11, wherein:
    said sampling system comprises an electrically driven pumping element, with a bellows actuated by a pressing magnet.

14. A breath alcohol measuring device in accordance with claim 10, wherein:
said evaluating and control unit has a signal connection on said output side to selectively release and block operation of a machine or device connected to the breath alcohol measuring device.

15. A breath alcohol measuring device in accordance with claim 11, wherein:
said evaluating and control unit has a signal connection on said output side to selectively release and block operation of a starter of a driving engine of a motor vehicle, aircraft or watercraft.

16. A breath alcohol measuring device in accordance with claim 14, wherein:
said machine or device connected to the breath alcohol measuring device is a starter of a driving engine of a motor vehicle, aircraft or watercraft.

17. A breath alcohol measuring device in accordance with claim 10, wherein:
said breath alcohol sensor is one of an electrochemical, semiconductor or infrared optical sensor.

18. A device for measuring breath alcohol, the device comprising:
a flow chamber receiving exhaled breathing gas flow of a person being tested;
a flow diaphragm arranged in said flow chamber for flow through said flow diaphragm from an upstream side of said flow diaphragm to a downstream side of said flow diaphragm;
a first gas line in communication with an interior space of said flow chamber upstream of said flow diaphragm;
a breath alcohol sensor in communication with an interior space of said flow chamber downstream of said flow diaphragm;
a second gas line in communication with said breath alcohol sensor;
a differential pressure sensor bridging over said flow diaphragm, a first measuring connection of said differential pressure sensor being connected to said first gas line, a second measuring connection of said differential pressure sensor being connected through said second gas line and said breath alcohol sensor to said interior space of said flow chamber downstream of said flow diaphragm;
a throttling element arranged in said second gas line;
a sampling system connected to said second gas line, said sampling system creating a vacuum for drawing gas flow into said breath alcohol sensor and toward or into said second gas line; and
an evaluating and control unit connected on an input side to said pressure and alcohol sensors and receiving measured signals of said sensors, said evaluating and control unit being connected on an output side to said sampling system for controlling said sampling system and said evaluating and control unit including means for generating a machine or device release/block signal and applying said device release/block signal to a machine or device signal connection on said output side, said machine or device release/block signal for selectively releasing or blocking operation of a machine or device.

* * * * *

UNITED STATES PATENT AND TRADEMARK OFFICE
CERTIFICATE OF CORRECTION

PATENT NO. : 7,329,390 B2 Page 1 of 1
APPLICATION NO. : 10/385796
DATED : February 12, 2008
INVENTOR(S) : Stock et al.

It is certified that error appears in the above-identified patent and that said Letters Patent is hereby corrected as shown below:

On Title page
item (73) should read
Assignee: Dräger Safety AG & Co. KGaA, Lübeck (DE)

Signed and Sealed this

Twentieth Day of May, 2008

JON W. DUDAS
*Director of the United States Patent and Trademark Office*